(12) United States Patent
Chang (10) Patent No.: US 10,842,426 B2
(45) Date of Patent: Nov. 24, 2020

(54) VITAL SIGN MONITORING APPARATUS

(71) Applicant: Kuo-Yuan Chang, New Taipei (TW)

(72) Inventor: Kuo-Yuan Chang, New Taipei (TW)

(*) Notice: Subject to any disclaimer, the term of this patent is extended or adjusted under 35 U.S.C. 154(b) by 97 days.

(21) Appl. No.: 16/158,902

(22) Filed: Oct. 12, 2018

(65) Prior Publication Data

US 2019/0046098 A1    Feb. 14, 2019

Related U.S. Application Data

(63) Continuation-in-part of application No. 14/539,518, filed on Nov. 12, 2014, now abandoned.

(30) Foreign Application Priority Data

Aug. 19, 2014    (TW) .............................. 103214807 A (51) Int. Cl.

| | |
|---|---|
| *A61B 5/15* | (2006.01) |
| *A61B 5/0205* | (2006.01) |
| *A61B 5/00* | (2006.01) |
| *G16H 40/63* | (2018.01) |
| *A61B 5/1455* | (2006.01) |
| *A61B 5/145* | (2006.01) |
| *G16H 10/60* | (2018.01) |
| *A61B 5/021* | (2006.01) |
| *G16H 40/60* | (2018.01) |

(52) U.S. Cl.
CPC ...... *A61B 5/150786* (2013.01); *A61B 5/0205* (2013.01); *A61B 5/742* (2013.01); *G16H 40/63* (2018.01); *A61B 5/0008* (2013.01); *A61B 5/0022* (2013.01); *A61B 5/021* (2013.01); *A61B 5/14532* (2013.01); *A61B 5/14551* (2013.01); *A61B 5/746* (2013.01); *A61B 2562/08* (2013.01); *G16H 10/60* (2018.01); *G16H 40/60* (2018.01)

(58) Field of Classification Search
None
See application file for complete search history.

(56) References Cited

U.S. PATENT DOCUMENTS 5,361,755 A * 11/1994 Schraag ............... A61B 5/0011
                                                            600/300
6,454,708 B1 * 9/2002 Ferguson ............. A61B 5/6831
                                                            600/300

(Continued)

*Primary Examiner* — Carl H Layno
*Assistant Examiner* — Dacheng Xie
(74) *Attorney, Agent, or Firm* — Muncy, Geissler, Olds & Lowe, P.C.

(57) ABSTRACT

A vital sign monitoring apparatus includes a bar code list and a vital sign monitor. The bar code list includes determination bar codes and setting bar codes. The vital sign monitor includes a host computer and a bar code reader. The bar code reader reads at least one of the determination bar codes and the setting bar codes. The host computer includes a control unit, a transmission device and an intelligent memory device. The control unit is electrically connected with the bar code reader and a plurality of vital sign information input instruments. While reading the determination or setting bar code, the bar code reader generates an output signal. The intelligent memory device compares the output signal with the preset data to generate an action instruction. According to the action instruction, the control unit turns on/off the vital sign information input instruments or sets up the vital sign monitor.

15 Claims, 5 Drawing Sheets

(56) References Cited

U.S. PATENT DOCUMENTS

| | | | | |
|---|---|---|---|---|
| 2003/0163399 A1* | 8/2003 | Harper | ............... | G06Q 10/0635 |
| | | | | 705/35 |
| 2009/0177068 A1* | 7/2009 | Stivoric | ................ | A61B 5/01 |
| | | | | 600/365 |
| 2010/0056883 A1* | 3/2010 | Meschisen | ............ | G16H 40/40 |
| | | | | 600/301 |
| 2011/0068928 A1* | 3/2011 | Riley | ................ | A61B 5/6892 |
| | | | | 340/573.1 |
| 2011/0160547 A1* | 6/2011 | Yang | ................ | A61B 5/0002 |
| | | | | 600/301 |
| 2014/0276549 A1* | 9/2014 | Osorio | ............... | A61M 5/1723 |
| | | | | 604/503 |
| 2015/0119725 A1* | 4/2015 | Martin | ............... | A61B 5/04012 |
| | | | | 600/479 |
| 2015/0205947 A1* | 7/2015 | Berman | ............... | A61B 5/0031 |
| | | | | 726/16 |

* cited by examiner

| Test Item | Bar Code | Content |
|---|---|---|
| PR03-RPRO | | Urinary Protein |
| PR04-UGLU | | Urinary Sugar |
| PR05-EDEMA | | Edema |
| PR06-WEIGHT | | Body Weight |
| PR07-UKET | | Urinary Ketone |
| PR08-BGLU | | Blood Glucose |
| PR09-HEIGHT | | Height |
| PR10-PAIN | | Pain Index |
| PR11-STOOL | | Stool Volume |

Fig. 5

VITAL SIGN MONITORING APPARATUS

CROSS REFERENCE TO RELATED APPLICATIONS

This application is a continuation-in-part of U.S. patent application Ser. No. 14/539,518, filed Nov. 12, 2014, and entitled "VITAL SIGN MONITORING APPARATUS;" and this application claims priority of Application No. 103214807 filed in Taiwan on 19 Aug. 2014 under 35 U.S.C. § 119; The aforementioned related application is hereby incorporated by reference in its entirety.

BACKGROUND OF THE INVENTION

1. Field of the Invention

The present invention relates to a vital sign monitoring apparatus, particularly to a vital sign monitoring apparatus, which can scan determination bar codes or setting bar codes for detecting vital sign information or setting up the functions of the vital sign monitoring apparatus.

2. Description of the Prior Art

The medical apparatuses grow more and more advanced nowadays. In order to obtain and monitor vital signs of patients, various vital sign monitors are arranged in the clinics, emergency units, intensive care units and general wards of hospitals. At present, the vital sign monitors are mainly used to measure body temperature, blood pressure and blood oxygen. The measurement results are presented on the screens of the vital sign monitors and recorded by medical personnel if necessary. Some vital sign monitors can alert the medical personnel while the vital sign value of a patient is abnormal. If the medical personnel is not in the nearby of the patient, they may fail to treat the patient timely, however.

Body temperature, blood pressure and blood oxygen can be measured with special instruments, such as clinical thermometers, blood pressure meters and oximeters. The medical personnel also have to consider measuring the following vital signs according to the condition of a patient, including urine volume, stool volume, pain index, food intake, fluid infusion and edema, which were recorded by medical personnel manually in the past. The modern hospitals normally adopt electronic anamneses and use electronic vital sign monitors to automatically transmit vital sign data of patients. However, most of the vital signs still need to be examined, transcribed and then input into computers by medical personnel manually. Thus, medical personnel have to spend time in transcribing and inputting vital sign data with the likelihood of inaccurate manual transcription and erroneous vital sign data transference.

SUMMARY OF THE INVENTION

In order to solve the abovementioned problems, a vital sign monitoring apparatus is provided to include a bar code list and a vital sign monitor. The bar code list includes a plurality of determination bar codes and a plurality of setting bar codes. The vital sign monitor further includes a host computer and a bar code reader. The bar code reader reads at least one of the determination bar codes and the setting bar codes. The host computer includes a control unit, a transmission device and an intelligent memory device, wherein the transmission device and the intelligent memory device are electrically connected with the control unit. The intelligent memory device contains preset data and a plurality of action instructions, wherein the action instructions are respectively corresponding to the determination bar codes and the setting bar codes. The control unit is also electrically connected with the bar code reader, a blood pressure measurement instrument and a plurality of vital sign information input instruments. The blood pressure measurement instrument is used to measure blood pressure and acquire blood pressure information. The vital sign information input instruments are respectively corresponding to the determination bar codes and respectively detect different vital sign information. While reading any one of the determination bar codes, the bar code reader generates a first output signal corresponding to the determination bar code and transmits the first output signal to the intelligent memory device. After receiving the first output signal, the intelligent memory device compares the first output signal with the preset data and generates a first action instruction to the control unit. According to the first action instruction, the control unit receives vital sign information from at least one of the vital sign information input instruments. The transmission device transmits the detected vital sign information to a database. While reading any one of the setting bar codes, the bar code reader generates a second output signal corresponding to the setting bar code and transmits the second output signal to the intelligent memory device. The intelligent memory device compares the second output signal with the preset data and generates a second action instruction to the control unit. According to the second action instruction, the control unit sets up the functions of the vital sign monitor. The first action instructions at least contain an instruction for monitoring the pain index. The second action instructions at least contain settings for wireless transmission and wireless linking to make the vital sign monitor function as a wireless router.

DESCRIPTION OF THE PREFERRED EMBODIMENTS

The present invention will be described in detail with embodiments and attached drawings below. However, these embodiments are only to exemplify the present invention but not to limit the scope of the present invention. In addition to the embodiments described in the specification, the present invention also applies to other embodiments. Further, any modification, variation, or substitution, which can be easily made by the persons skilled in that art according to the embodiment of the present invention, is to be also included within the scope of the present invention, which is based on the claims stated below. Although many special details are provided herein to make the readers more fully understand the present invention, the present invention can still be practiced under a condition that these special details are partially or completely omitted. Besides, the elements or steps, which are well known by the persons skilled in the art, are not described herein lest the present invention be limited unnecessarily. Similar or identical elements are denoted with similar or identical symbols in the drawings. It should be noted: the drawings are only to depict the present invention schematically but not to show the real dimensions or quantities of the present invention. Besides, matterless details are not necessarily depicted in the drawings to achieve conciseness of the drawings.

Figure 1:
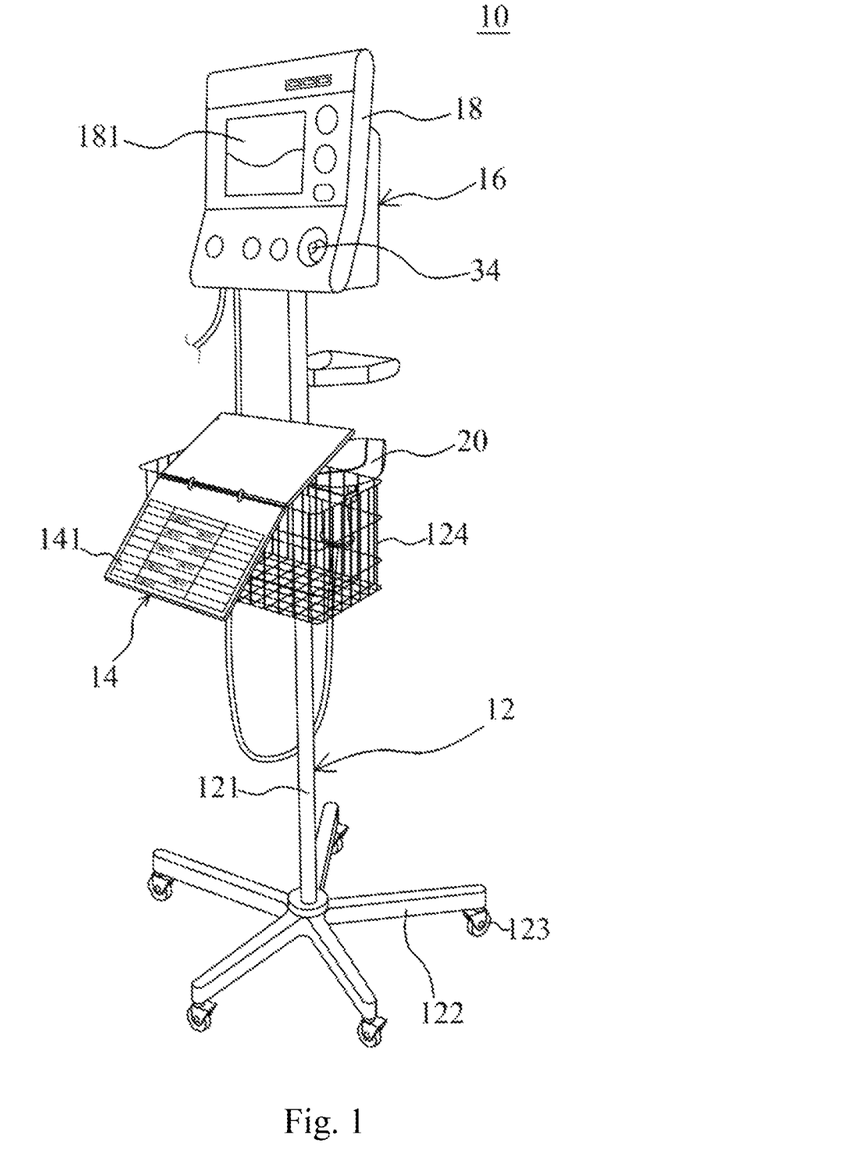
FIG. 1 is a diagram schematically showing the structure of a vital sign monitoring apparatus according to one embodiment of the present invention.

Refer to FIG. 1 a diagram schematically showing the structure of a vital sign monitoring apparatus according to one embodiment of the present invention. The vital sign monitoring apparatus 10 includes a frame 12, a bar code list 14 and a vital sign monitor 16. In one embodiment, the frame 12 may further include a longitudinal rod 121, a fixing seat 122 connected with the bottom of the longitudinal rod 121, wheels 123 arranged on the legs of the fixing seat 122, and a rack 124 arranged on an appropriate position of the middle section of the longitudinal rod 121. According to requirement, on the rack 124 may be placed the bar code reader 20 and measurement accessories (not shown in the drawings), such as the cuff for blood pressure measurement, the thermometer of temperature measurement, the lancets for blood glucose measurement, the sensor for electrocardiography measurement, and the sensor for blood oxygen measurement.

The bar code list 14 contains a plurality of determination bar codes and a plurality of setting bar codes. In one embodiment, the bar code list 14 includes a plurality of cardboards 141, and the bar code list 14 is hanged on the rack 124. In the embodiment shown in FIG. 1, the bar code list 14 is exemplarily arranged on one side of the frame 12. However, the present invention is not limited by the embodiment. The bar code list 14 may be disposed in any place of the frame 12 according to requirement.

Figure 2:
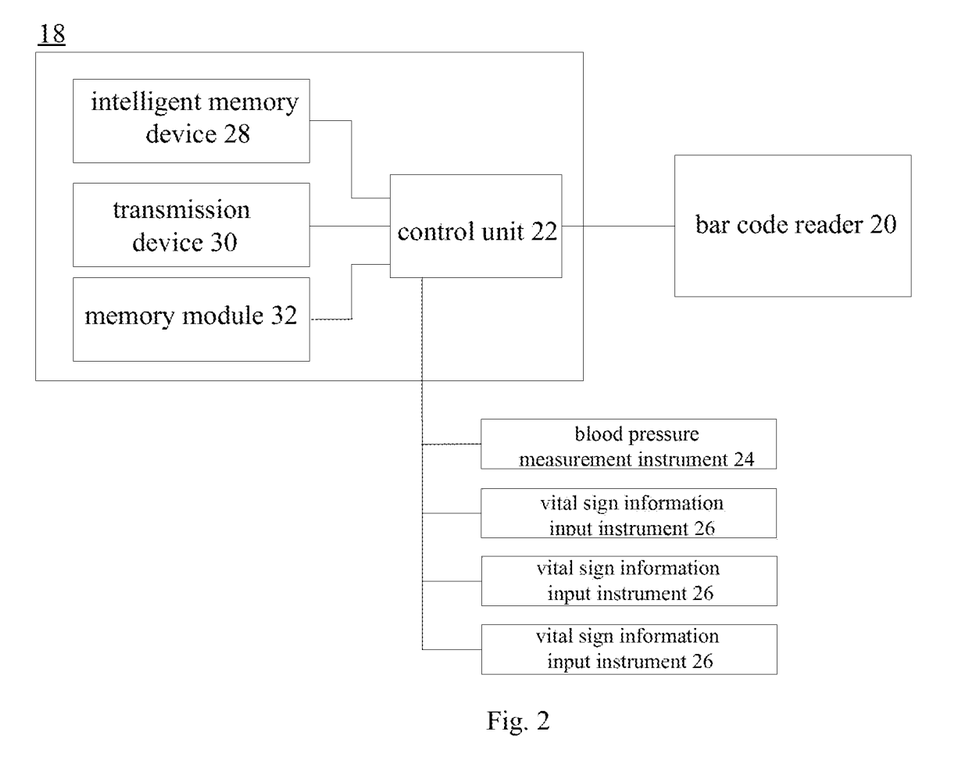
FIG. 2 is a block diagram schematically showing a vital sign monitoring apparatus according to one embodiment of the present invention.

The vital sign monitor 16 includes a host computer 18 and a bar code reader 20. The host computer 18 may be mounted on the frame 12. The bar code reader 20 is used to read at least one of the determination bar codes and the setting bar codes. Refer to FIG. 2 a block diagram schematically showing the structure of a vital sign monitor according to one embodiment of the present invention. The host computer 18 includes, a display 181, a control unit 22, a transmission device 30 electrically connected with the control unit 22, and an intelligent memory device 28 also electrically connected with the control unit 22. The intelligent memory device 28 contains preset data and a plurality of action instructions, wherein the action instructions are respectively corresponding to the determination bar codes and the setting bar codes. The signal transmission between the elements will be described in detail below.

Refer to FIG. 2 again. The control unit 22 is also electrically connected with the bar code reader 20, a blood pressure measurement instrument 24 and a plurality of vital sign information input instruments 26. The blood pressure measurement instrument 24 together with a cuff is used to measure the blood pressure of a patient. The vital sign information input instruments 26 are respectively corresponding to the determination bar codes and respectively used to measure different vital signs. In one embodiment, one or more vital sign measurement instruments are built in the host computer 18, and the function of the host computer 18 is expandable via linking with other external vital sign measurement instruments.

Figure 3:
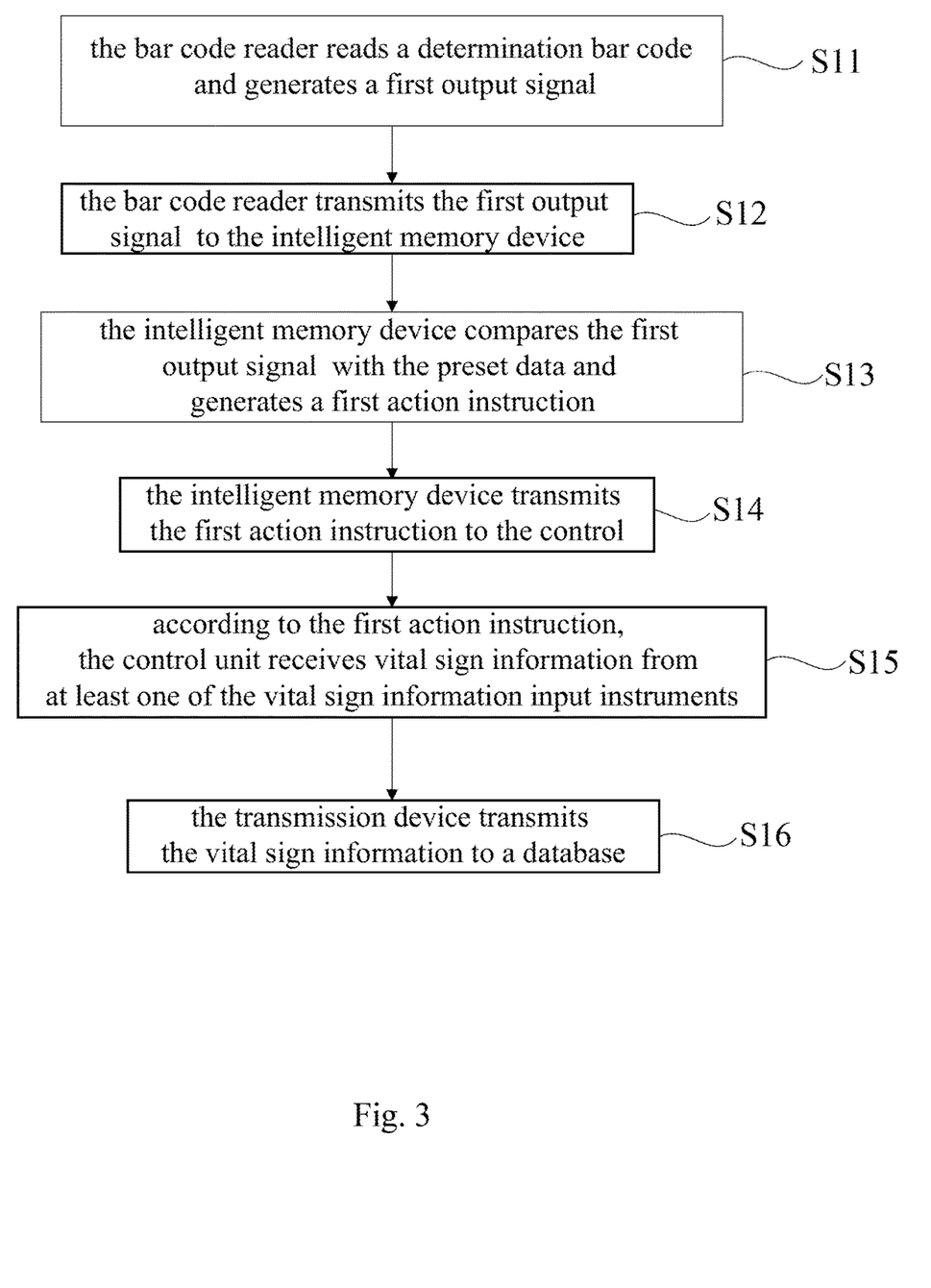
FIG. 3 is a diagram schematically showing a flowchart of signal transmission according to one embodiment of the present invention.

FIG. 3 is a diagram schematically showing a flowchart of signal transmission according to one embodiment of the present invention. Refer to FIGS. 1-3 simultaneously. While a user reads a determination bar code of the bar code list 14 with the bar code reader 20, the bar code reader 20 generates a first output signal corresponding to the determination bar code and transmits the first output signal to the intelligent memory device 28 (Step S11 and Step S12). The intelligent memory device 28 compares the first output signal with the preset data and generates a first action instruction to the control unit 22 (Step S13 and Step S14). According to the first action instruction, the control unit 22 receives vital sign information from at least one of the vital sign information input instruments (Step S15). The transmission device 30 transmits the detected vital sign information to a database (Step S16).

Figure 5:
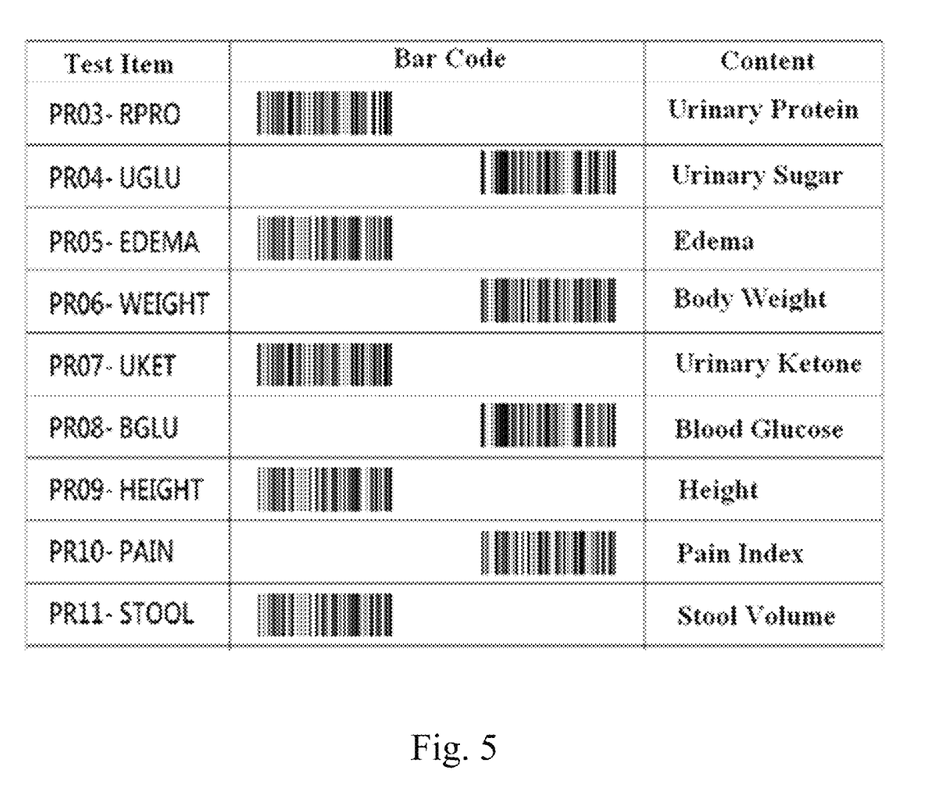
FIG. 5 shows a plurality of determination bar codes according to one embodiment of the present invention.

In one embodiment, the first action instructions include an instruction of monitoring pain indexes. The first action instructions may further include instructions of monitoring urinary protein, urinary sugar, urinary ketone, blood glucose, blood oxygen, body temperature, body weight, body height, electrocardiography, stool volume, and edema. FIG. 5 shows a plurality of determination bar codes according to one embodiment of the present invention.

In one embodiment, the vital sign information input instruments may include a blood oxygen measurement instrument, an electrocardiography measurement instrument, a clinical thermometer, a keyboard, or turning knobs.

In one embodiment, while the user reads a determination bar code containing an instruction of monitoring pain indexes with the bar code reader 20, the measurement instruction corresponding to the determination bar code will be displayed on the display 181 of the host computer 18 for the user to select or set. After the selection or setting is determined by the user, an output signal of monitoring pain indexes corresponding to the instruction of monitoring pain indexes is generated and transmitted to the intelligent memory device 28. The intelligent memory device 28 compares the output signal of monitoring pain indexes with the preset data and generates an action instruction of monitoring pain indexes to the control unit 22. According to the action instruction of monitoring pain indexes, the control unit 22 receives the vital sign information of pain indexes, which are rated by a pain rating index (PRI) and input by the user using a keyboard. Then, the transmission device 30 transmits the vital sign information of pain indexes to the database.

In one embodiment, while the bar code reader 20 reads a determination bar code containing an instruction of monitoring blood glucose, the measurement instruction corresponding to the determination bar code will be displayed on the display 181 of the host computer 18. At the same time, an output signal of monitoring blood glucose corresponding to the instruction of monitoring blood glucose is generated and transmitted to the intelligent memory device 28. The intelligent memory device 28 compares the output signal of monitoring blood glucose with the preset data and generates an action instruction of monitoring blood glucose to the control unit 22. According to the action instruction of monitoring blood glucose, the control unit 22 communicates with a blood glucose measurement instrument (including a lancet) and receives vital sign information of blood glucose of the testee. Then, the transmission device 30 transmits the vital sign information of blood glucose to the database.

Figure 4:
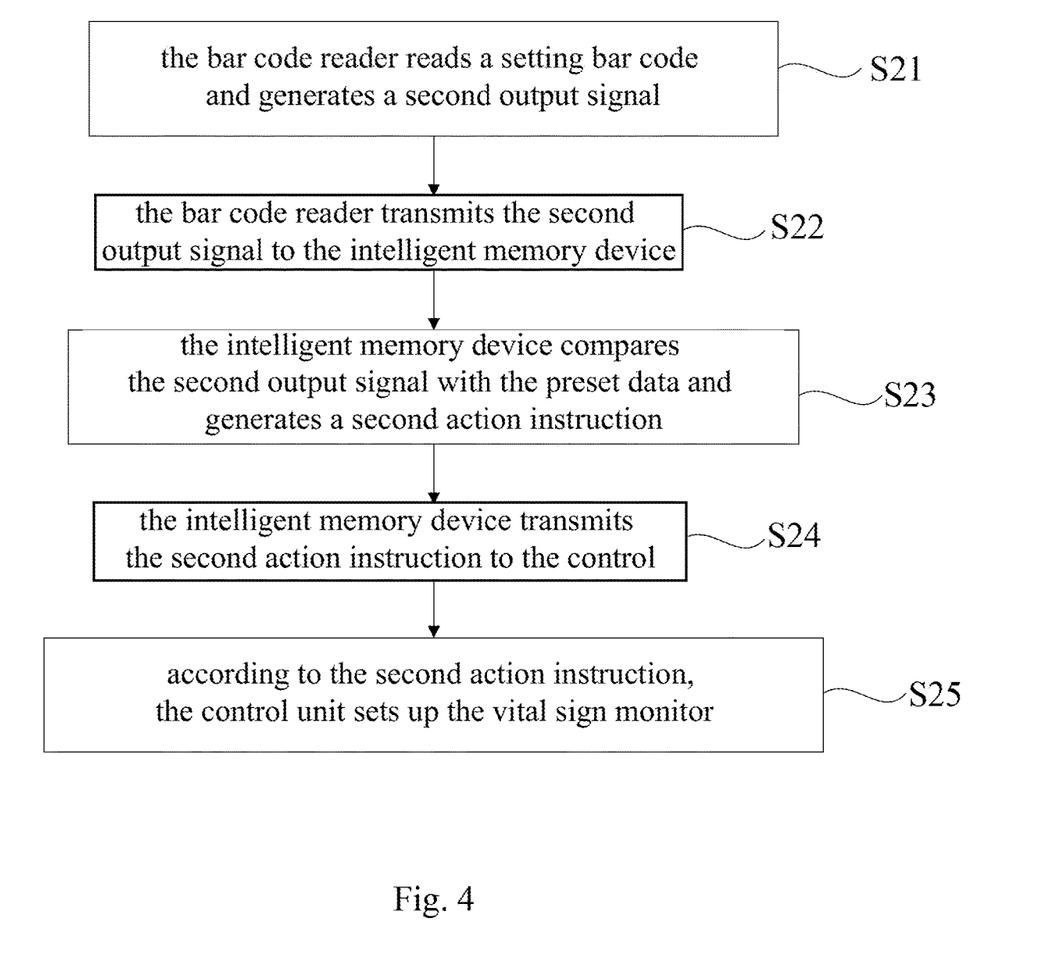
FIG. 4 is a diagram schematically showing a flowchart of signal transmission according to another embodiment of the present invention.

FIG. 4 is a diagram schematically showing a flowchart of signal transmission according to another embodiment of the present invention. Refer to FIG. 1, FIG. 3, and FIG. 4 simultaneously. While reading a setting bar code of the bar code list 14, the bar code reader 20 generates a second output signal corresponding to the setting bar code and transmits the second output signal to the intelligent memory device 28 (Step S21 and Step S22). The intelligent memory device 28 compares the second output signal with the preset data and generates a second action instruction to the control unit 22 (Step S23 and Step S24). According to the second action instruction, the control unit 22 sets up the vital sign monitor (Step S25).

The transmission device 30 may be a device with a wired transmission interface, such as a USB port or an RS232 port. Alternatively, the transmission device 30 may be a device with a wireless transmission interface, such as a 2.4G RF transmission interface, a GSM/UMTS/LTE mobile communication interface, or a WiFi transmission interface. The vital sign monitor further displays a linking information or a transmission information while the transmission device transmits the vital sign information to the database, and wherein the linking information includes at least one of linking in success or failure, and the transmission information includes at least one of transmission in success or failure. The vital sign monitor further displays one or more of following statuses: transmission completion, transmission failure, transmission ready, link and unlink in different text or symbols, while the transmission device transmits the detected vital sign information to the database, and all transmission signals are encrypted for information security.

Through the transmission device 30, the detected vital sign values are transmitted to the database. The vital sign monitor 16 may display one or more of the following statuses: transmission completion, transmission failure, transmission ready, link, and unlink, in different text or symbols. In one embodiment, all the transmission signals are encrypted for information security.

In one embodiment, the second action instructions at least include the settings of wireless transmission and wireless link, whereby the vital sign monitor 16 may function as a wireless router. The second action instructions may further include a resetting instruction, a volume setting instruction, a pressure setting instruction, a screen brightness setting instruction, a software setting instruction, a user setting instruction, a precision setting instruction, and a database setting instruction.

In one embodiment, while reading the setting bar codes containing a resetting instruction, the bar code reader 20 generates an output signal of resetting and transmits the output signal of resetting to the intelligent memory device 28. The intelligent memory device 28 compares the output signal of resetting with the preset data and generates an action signal of resetting to the control unit 22. According to the action signal of resetting, the control unit 22 turns off the vital sign monitor 16 or turns off the vital sign information input devices, which are originally opened.

In one embodiment, while reading the setting bar code containing a wireless transmission setting instruction and a wireless link setting instruction, the bar code reader 20 generates an output signal of wireless setting and transmits the output signal of wireless setting to the intelligent memory device 28. The intelligent memory device 28 compares the output signal of wireless setting with the preset data and generates an action signal of wireless setting to the control unit 22. According to the action signal of wireless setting, the control unit 22 turns on the wireless network of the vital sign monitor to make the vital sign monitor 16 function as a wireless router. Thereby, the user may wirelessly links to the vital sign monitor through a smart phone and undertake internal settings of the vital sign monitor. While the bar code reader 20 reads a setting bar code of adding a new function, the vital sign monitor is expanded to receive more types of vital signs, such as the respiratory rate.

In another embodiment, the second action instructions further include an action instruction of memory setting for storing at least one of the first action instructions of the determination bar code into the intelligent memory device 28 while the bar code reader 20 reads the setting bar code and generates an output signal of memory setting, such that is convenient for the user to next time directly measure with the vital sign monitor 16 without reading the determination bar codes again with the bar code reader 20. For example, when the bar code reader 20 sequentially reads the fast-determination bar codes including monitoring pain indexes and body weight and then the setting bar codes including the setting instruction of memory setting, these action instructions may be stored in the intelligent memory device. Moreover, the determination instructions corresponding to these stored action instructions will be displayed on a display of the host computer when the use uses the vital sign monitor next time, so that the user may directly do a measurement without reading the determination bar codes again. The second action instructions further include an action instruction of cleaning setting for cleaning at least one of the first action instructions stored in the intelligent memory device 28 while the bar code reader 20 reads the setting bar code and generates an output signal of cleaning setting.

In one embodiment, the bar code list 14 at least includes fast-determination bar codes and fast-cleaning bar codes. While reading a fast-determination bar code of the bar code list 14, the bar code reader 20 stores a fast-select option corresponding to the fast-determination bar code to the intelligent memory device 28. While the user uses the vital sign monitor 16 next time, the user may conveniently transmit the first action instructions, which are sequentially corresponding to the fast-select options in the intelligent memory device 28, to the control unit 22. According to the first action instruction, the control unit 22 receives the vital sign values, which are input by the user using a keyboard or turning knobs. Then, the transmission device 30 transmits the input vital sign information to the database.

In one embodiment, while reading the fast-determination bar codes including the fast-determination bar codes of monitoring pain indexes and body weight, the measurement instructions corresponding to the fast-determination bar codes will be displayed on the display 181 of the host computer 18 and stored to the intelligent memory device 28 at the same time. While the user uses the vital sign monitor 16 next time, the control unit 22 receives the vital sigh values of pain indexes and body weight, which are input manually by the user using a keyboard or turning knobs, according to the first action instructions that are sequentially corresponding to the fast-determination options in the intelligent memory device 28. Then, the transmission device 30 transmits the input vital sign information to the database.

The present invention uses the transmission device 30 to transmit the detected vital sign information to the database to exempt the medical personnel from transcribing and inputting vital sign data and reduce the likelihood of inaccurate manual transcription and erroneous vital sign data transference. In the present invention, the database may be a cloud database, a Hospital Information System (HIS), or a Nursing Information System (NIS). The database can consolidate the data and automatically check whether the vital sign value is a critical value according to a standard; the vital sign information or the critical value is automatically reported in a wired or wireless method, such as email, Short Message Service (SMS), or Multimedia Messaging Service (MMS).

Refer to FIG. 2 again. The host computer 18 further includes a memory module 32 electrically connected with the control unit 22 and used to store the blood pressure information detected by the blood pressure measurement instrument 24 or the vital sign information detected by the vital sign information input instruments 26. The memory module 32 may include an external storage device, which is a memory chip or a memory card. In one embodiment, the vital sign monitor 16 further includes a portable electronic device (not shown in the drawing). The portable electronic device may be electrically connected with the control unit 22 and used to store the blood pressure information detected by the blood pressure measurement instrument 24 or the vital sign information detected by the vital sign information input instruments 26.

In the present invention, the user may manually input the measurement instructions and the function-setting instructions via using a turning knob 34 on the host computer 18, in addition to via using the bar code reader 20. The host computer 18 also has LED alert lights for providing alert signals.

In the present invention, the vital sign monitor and the bar code list may be placed on the mobile frame, whereby the vital sign monitoring apparatus can be conveniently moved to different wards. Further, the vital sign monitoring apparatus of the present invention can function flexibly and can execute different measurement instructions and different function-setting instructions according to the requirements of different wards. The medical personnel only need to scan the corresponding bar code to the host computer before they intend to undertake a vital sign measurement or input the detected vital sign values. The vital signs monitored for different patients are different. For example, pain index measurement is necessary for the patients in cancer wards, but it may be unnecessary for the patients in general wards. The vital sign monitoring apparatus of the present invention uses the bar code reader to selectively scan the determination bar codes or the setting bar codes according to the requirements of patients, whereby to avoid setting numerous measurement functions in an identical vital sign monitoring apparatus and exempt medical personnel from the inconvenience of selecting among many instructions.

The abovementioned embodiments are used to demonstrate the technical thought and characteristics of the present invention to enable the persons skilled in the art to understand, make, and use the present invention. However, these embodiments are only to exemplify the present invention but not to limit the scope of the present invention. Any equivalent modification or variation according to the spirit of the present invention is to be also included by the scope of the present invention.

What is claimed is:

1. A vital sign monitoring apparatus comprising:
   a bar code list including a plurality of determination bar codes and a plurality of setting bar codes;
   a vital sign monitor including a host computer and a bar code reader used to read at least one of the determination bar codes and the setting bar codes, wherein the host computer further includes:
   a control unit electrically connected with the bar code reader and respectively connected with a blood pressure measurement instrument and a plurality of vital sign information input instruments, wherein the blood pressure measurement instrument detects blood pressure information, and wherein the vital sign information input instruments are respectively corresponding to the determination bar codes and detect different vital sign information;
   a transmission device electrically connected with the control unit; and
   an intelligent memory device electrically connected with the control unit and containing preset data and a plurality of action instructions, wherein the action instructions are respectively corresponding to the determination bar codes and the setting bar codes, and
   wherein while reading any one of the determination bar codes, the bar code reader generates a first output signal corresponding to the determination bar code and transmits the output signal to the intelligent memory device, and wherein the intelligent memory device compares the first output signal with the preset data to generate a first action instruction to the control unit, and wherein according to the first action instruction, the control unit receives vital sign information from at least one of the vital sign information input instruments, and the transmission device transmits the vital sign information to a database; and
   wherein while reading any one of the setting bar codes, the bar code reader generates a second output signal corresponding to the setting bar code and transmits the second output signal to the intelligent memory device, and wherein the intelligent memory device compares the second output signal with the preset data to generate a second action instruction to the control unit, and wherein according to the second action instruction, the control unit sets up functions of the vital sign monitor, and
   wherein the first action instructions at least include an instruction of monitoring pain indexes, and
   wherein the second action instructions at least include instructions of wireless transmission and wireless linking to turn on a wireless network of the vital sign monitor to make the vital sign monitor be as a wireless router, and
   wherein the first action instructions further include instructions of monitoring urinary protein, urinary sugar, urinary ketone, blood glucose, blood oxygen, body temperature, body weight, body height, electrocardiography, stool volume, and edema.

2. The vital sign monitoring apparatus according to claim 1, wherein the vital sign information input instruments include a blood oxygen measurement instrument, an electrocardiography measurement instrument, a clinical thermometer, a keyboard, or turning knobs.

3. The vital sign monitoring apparatus according to claim 1, wherein the second action instructions include an action instruction of resetting, and wherein while reading the setting bar code, the bar code reader generates an output signal of resetting and transmits the output signal of resetting to the intelligent memory device, and wherein the intelligent memory device compares the output signal of resetting with the preset data to generate the action instruction of resetting to the control unit, and wherein according to the action instruction of resetting, the control unit turns off the vital sign monitor.

4. The vital sign monitoring apparatus according to claim 1, wherein the second action instructions further include an action instruction of memory setting for storing at least one of the first action instructions of the determination bar code into the intelligent memory device while the bar code reader reads the setting bar code and generates an output signal of memory setting.

5. The vital sign monitoring apparatus according to claim 4, wherein the second action instructions further include an action instruction of cleaning setting for cleaning at least one of the first action instructions stored in the intelligent memory device while the bar code reader reads the setting bar code and generates an output signal of cleaning setting.

6. The vital sign monitoring apparatus according to claim 1, wherein the second action instructions further include a volume setting instruction, a pressure setting instruction, a screen brightness setting instruction, a software setting instruction, a user setting instruction, a precision setting instruction, or a database setting instruction.

7. The vital sign monitoring apparatus according to claim 1 further comprising a portable electronic device, wherein the portable electronic device is electrically connected with the control unit to store the blood pressure information detected by the blood pressure measurement instrument or the vital sign information detected by the vital sign information input instruments.

8. The vital sign monitoring apparatus according to claim 1, wherein the host computer further comprises a memory module, wherein the memory module is electrically connected with the control unit to store the blood pressure information detected by the blood pressure measurement instrument or the vital sign information detected by the vital sign information input instruments, and wherein the memory module includes an external storage device with a memory chip or a memory card.

9. The vital sign monitoring apparatus according to claim 1, wherein the vital sign monitor further displays a linking information or a transmission information while the transmission device transmits the vital sign information to the database, and wherein the linking information includes at least one of linking in success or failure, and the transmission information includes at least one of transmission in success or failure.

10. The vital sign monitoring apparatus according to claim 1, wherein the vital sign monitor further displays one or more of following statuses: transmission completion, transmission failure, transmission ready, link and unlink in different text or symbols, while the transmission device transmits the detected vital sign information to the database, and wherein all transmission signals are encrypted for information security.

11. The vital sign monitoring apparatus according to claim 1, wherein the bar code list further comprises at least one fast-determination bar code and at least one fast-cleaning bar code, and wherein the bar code reader stores a fast-select option corresponding to the fast-determination bar code to the intelligent memory device while reading the fast-determination bar code of the bar code list, and wherein the first action instructions corresponding to the fast-select options in the intelligent memory device are directly transmitted to the control unit while the vital sign monitor is used next time.

12. The vital sign monitoring apparatus according to claim 11, wherein the fast-determination bar codes comprise the fast-determination bar codes of monitoring pain indexes and body weight, and wherein at least one measurement instruction corresponding to the fast-determination bar codes is displayed on a display of the host computer and stored to the intelligent memory device at the same time, while the fast-determination bar codes including the fast-determination bar codes of monitoring pain indexes and body weight are read.

13. The vital sign monitoring apparatus according to claim 12, wherein the control unit receives the vital sigh values of pain indexes and body weight according to the first action instructions that are sequentially corresponding to the fast-determination options in the intelligent memory device when the vital sign monitor is used next time, and wherein the transmission device transmits an input vital sign information to the database.

14. The vital sign monitoring apparatus according to claim 1, wherein the second action instructions further include an action instruction of memory setting for storing at least one of the first action instructions of the determination bar code into the intelligent memory device while the bar code reader reads the setting bar code and generates an output signal of memory setting, such that a user next time directly measures with the vital sign monitor without reading the determination bar codes again with the bar code reader.

15. The vital sign monitoring apparatus according to claim 1, wherein the second action instructions further include an action instruction of cleaning setting for cleaning at least one of the first action instructions stored in the intelligent memory device while the bar code reader reads the setting bar code and generates an output signal of cleaning setting.

* * * * *